United States Patent [19]
Charters

[11] Patent Number: 5,916,151
[45] Date of Patent: Jun. 29, 1999

[54] APPARATUS FOR DILATING A BODY CAVITY

[76] Inventor: John Dumergue Charters, 8 Sayer Street, Midland, Western Australia, 6056, Australia

[21] Appl. No.: 08/913,149

[22] PCT Filed: Mar. 6, 1996

[86] PCT No.: PCT/AU96/00116

§ 371 Date: Sep. 5, 1997

§ 102(e) Date: Sep. 5, 1997

[87] PCT Pub. No.: WO96/27323

PCT Pub. Date: Sep. 12, 1996

[30] Foreign Application Priority Data

Mar. 7, 1995 [AU] Australia ................................. PN1594
Mar. 28, 1995 [AU] Australia ................................. PN1994

[51] Int. Cl.⁶ .................................................. A61M 29/00
[52] U.S. Cl. ......................... 600/224; 600/222; 606/198; 604/106
[58] Field of Search ..................................... 600/224, 225, 600/226, 222, 219, 220; 604/106; 606/198

[56] References Cited

U.S. PATENT DOCUMENTS 1,626,149  5/1927  Odell .
2,078,111  4/1937  Weeks ..................................... 604/106
2,083,573  4/1937  Morgan .
2,374,863  5/1945  Gutmann .

FOREIGN PATENT DOCUMENTS 0 043 218 A1  6/1980  European Pat. Off. .
0 288 157 A2  3/1988  European Pat. Off. .
2 635 451 A1  8/1988  France .
2 116 043  1/1983  United Kingdom .
WO 92/21279  12/1992  WIPO .
WO 94/12091  6/1994  WIPO .
WO 94/26344  11/1994  WIPO .

*Primary Examiner*—Michael H. Thaler
*Attorney, Agent, or Firm*—Holland & Hart LLP

[57] ABSTRACT

Apparatus for dilating a body cavity comprising at least two elongate elements positioned in generally side-by-side relationship. The elongate elements are movable laterally with respect to each other between a contracted condition wherein first end sections of the elongate elements are closely adjacent one another for insertion into the body cavity, and an expanded condition wherein the first end sections of the elongate elements are circumferentially spaced apart for dilating the body cavity. The elongate elements are arranged to normally occupy the contracted condition, and a control device is provided for selectively moving the elongate elements from the contracted condition to the expanded condition.

14 Claims, 7 Drawing Sheets

APPARATUS FOR DILATING A BODY CAVITY

TECHNICAL FIELD

The present invention relates to an apparatus for dilating a body cavity. In particular, the invention relates to a vaginal speculum for use in gynaecology.

BACKGROUND OF THE INVENTION

A vaginal speculum is used in gynaecology for various procedures including opening of the vaginal cavity for inspection of the uterine cervix and to carry out procedures such as a vaginal examination to obtain swabs and scrapings for a papanicolaou stain test, and to do a colposcopy.

A type of vaginal speculum commonly in use comprises a pair of broad dilator blades which are pivoted together and movable apart when inserted into the vaginal cavity to cause the vagina to dilate.

While such a vaginal speculum performs satisfactorily in many situations, it does have some disadvantages. One disadvantage is that each of the dilator blades presents a peripheral edge which can cause discomfort during insertion. A further disadvantage is that because of their broad nature the blades can obscure a significant part of the vaginal walls thereby obscuring matters of concern such as vaginal warts. A still further disadvantage is that the vaginal walls can urge the dilator blades together which can cause the blades to grip the cervix and thereby cause pain on removal of the speculum. A still further disadvantage is that the blades can pinch the vaginal wall when pivoted together prior to withdrawal of the speculum.

The present invention seeks to provide an apparatus for dilating a body cavity and in particular to provide a vaginal speculum which overcomes at least some of the disadvantages of the conventional speculum referred to above, or at least provides a useful alternative to such a speculum.

SUMMARY OF THE INVENTION

The invention provides an apparatus for dilating a body cavity comprising at least two elongate elements positioned in generally side-by-side relationship and movable laterally with respect to each other between a contracted condition wherein first end sections of the elongate elements are closely adjacent one another for insertion into the body cavity and an expanded condition wherein the first end sections of the elongate elements are circumferentially spaced apart for dilating the body cavity.

While there may be two or more of the elongate elements, it is particularly convenient that there be four such elements.

The elongate elements are each preferably firm yet resiliently flexible along the length thereof.

The elongate elements are preferably thin in profile and of circular or other rounded cross-section.

In the contracted position, the first end sections of the elongate elements are closely adjacent to present a compact shape for insertion into the body cavity.

In the expanded condition, the elongate elements define therebetween a central region of open-ended elongate shape through which gynaecological operations and procedures may be performed.

The elongate elements may be arranged to normally occupy one of the contracted or expanded conditions, a control means being provided for selectively moving the elongate elements from that one condition to the other condition. Conveniently, the elongate elements normally occupy the contracted condition and operation of the control means causes movement of the elongate elements from the contracted condition to the expanded condition.

The control means may comprise a control ring encircling the elongate elements and adjustment means extending between each elongate element and the control ring, the adjustment means being operable to move at least two of the elongate elements with respect to the control ring thereby moving the elongate elements from said one condition to the other condition. Preferably the adjustment means is operable to move all of the elongate elements with respect to the control ring.

The adjustment means may comprise a funicular element such as a cable laced between the control ring and the elongate elements whereby tensioning of the cable draws the elongate elements outwardly towards the ring.

The funicular element may be tensioned by any suitable means such as a tensioning device around which the funicular element can be wound for tensioning thereof. The tensioning device may have a locking means for selectively locking the tensioning device against rotation in the reverse direction to prevent unwinding of the funicular element.

The control means is preferably so positioned in relation to the elongate element that it is disposed exteriorly of the body cavity when the elongate elements are inserted therein.

The elongate elements may be retained in said side-by-side relationship by a retaining means. The retaining means may be disposed on a second end section of the elongate elements opposite to said first end section thereof.

The retaining means may comprise a closed loop. The closed loop may be of flexible construction. In particular, the closed loop may be resiliently flexible.

BRIEF DESCRIPTION OF THE DRAWINGS

The invention will be better understood by reference to the following description of several specific embodiments thereof as shown in the accompanying drawings in which.

DESCRIPTION OF PREFERRED EMBODIMENTS

Figure 1:
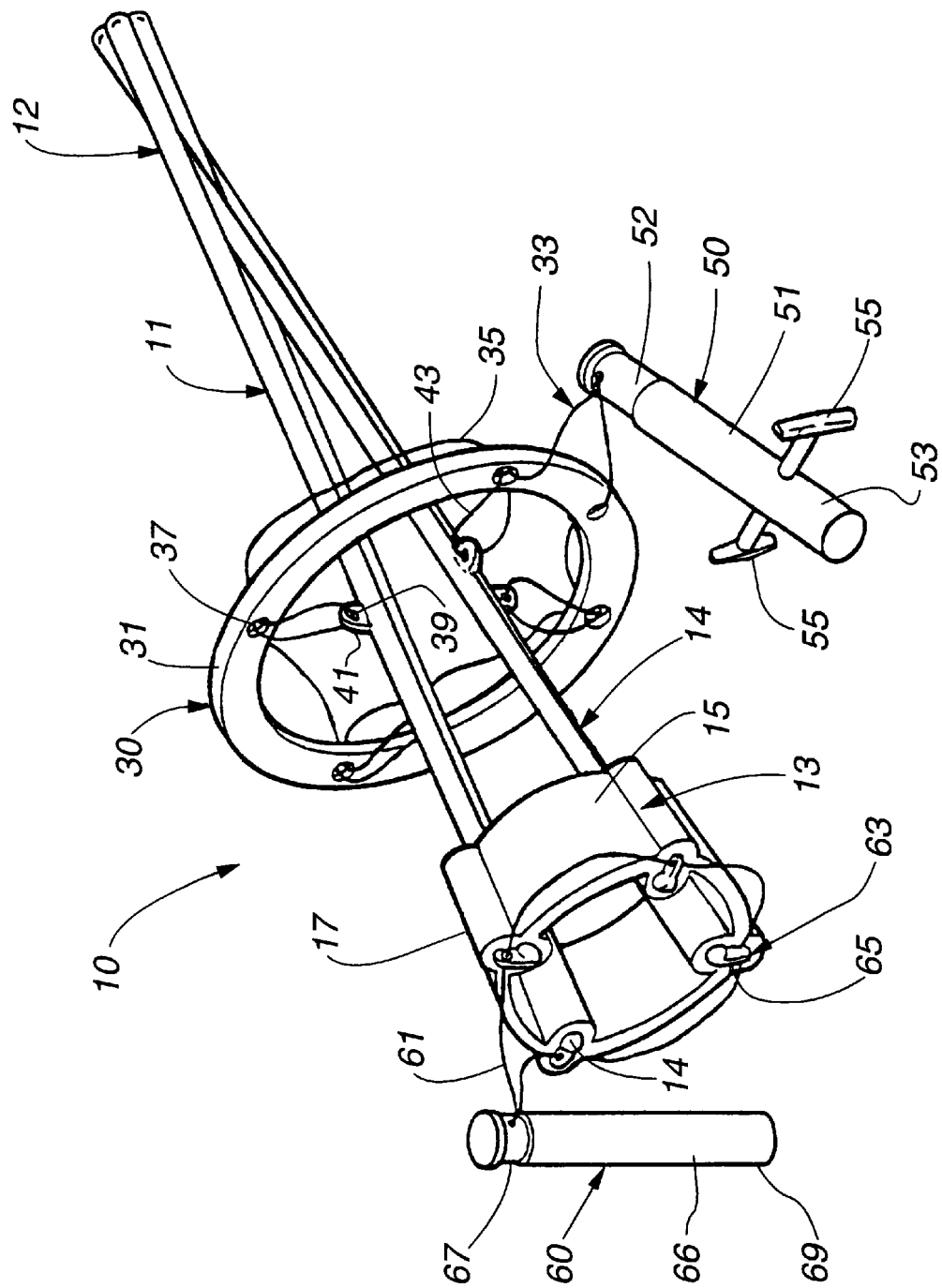
FIG. 1 is a perspective view of a vaginal speculum according to a first embodiment shown in a contracted condition.
Figure 2:
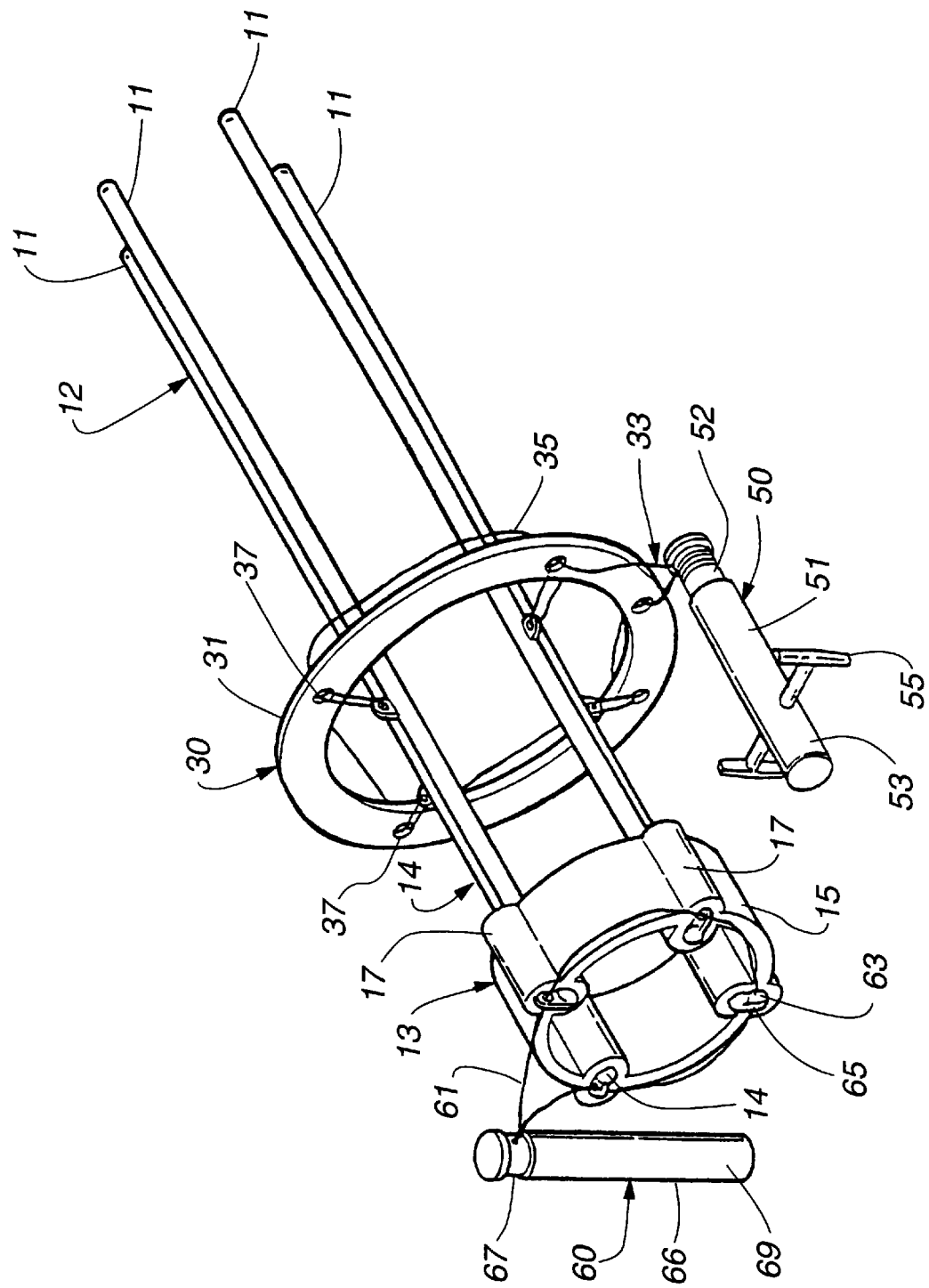
FIG. 2 is a perspective view similar to FIG. 1 with the exception that that the vaginal speculum is shown moving from the contracted condition to an expanded condition.

The first embodiment, which is shown in FIGS. 1 to 8 of the accompanying drawings, is directed to a vaginal speculum 10 comprising four elongate elements 11 of firm yet resiliently flexible construction.

The elongate elements 11 each have a first end section 12 and a second end section 14. Each elongate element 11 is thin in profile and of circular cross-section. The elongate elements 11 are positioned in side-by-side relationship and are linked one to another at the second end section 14 thereof by a retaining means 13. The retaining means 13 comprises a resiliently flexible band 15 having four integral sleeve portions 17 each for receiving and retaining the adjacent end section 14 of one of the elongate elements 11. The end section of each elongate element 11 extends beyond its respective sleeve portion 17, the purpose of which will be explained later.

Figure 3:
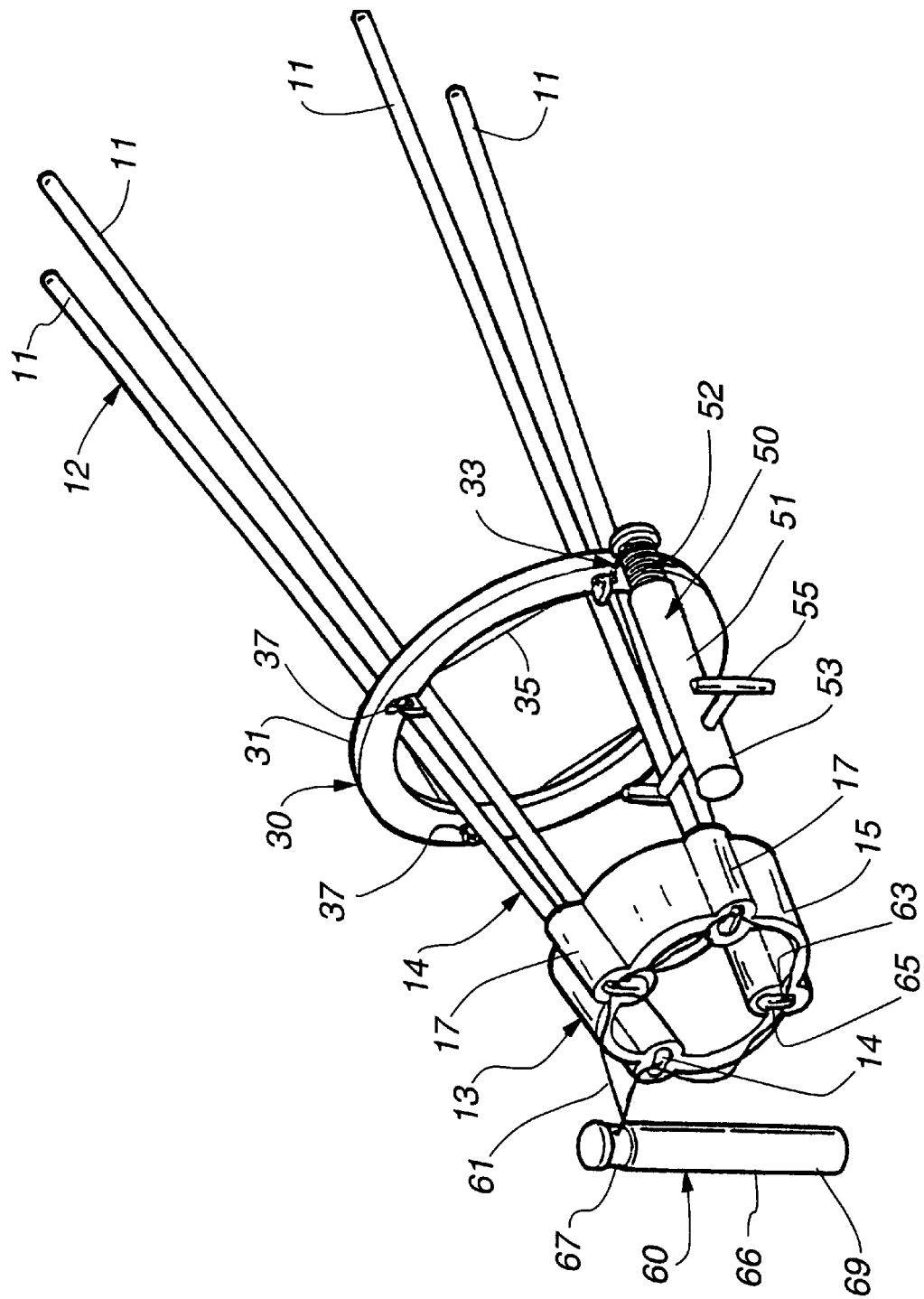
FIG. 3 is also a view similar to FIG. 1 with the exception that the vaginal speculum is shown in the expanded condition.

The retaining means 13 supports the elongate elements 11 in side-by-side relationship and allows them to move between a contracted condition in which the first end sections 12 of the elongate elements 11 are closely adjacent each other (as best seen in FIG. 1 of the drawings) to present a narrow shape for insertion into a vagina, and an expanded condition in which the elongate elements are circumferentially spaced apart (as best seen in FIG. 3 of the drawings) to define therebetween a central region of an open-ended elongate shape.

While in the side-by-side relationship the elongate elements 11 are also disposed angularly with respect to each other in the contracted condition to taper inwardly from the retaining means 13 to touch one another at the first end sections 12. Further, while in the side-by-side relationship the elongate elements 11 are also disposed angularly in the expanded condition to taper in the outward direction. The flexible nature of the retaining means 13 allows the elongate elements 11 to move angularly between the contracted and expanded conditions.

A control means 30 is provided for selectively moving the elongate elements from the contracted condition to the expanded condition. The control means is provided intermediate the ends of the elongate elements 11 at a location away from that first end sections 12 of the elongate elements 11 which are receivable in the vagina.

The control means 30 comprises a control ring 31 which encircles the elongate elements 11 and an adjustment means 33 operable between the control ring and the elongate elements for moving the elongate elements from the contracted condition to the expanded condition. The adjustment means 33 comprises a funicular element 35 in the form of a cable which is laced between a plurality of circumferentially spaced holes 37 provided in the control ring 31 and a hole 39 provided in a lug 41 on each elongate element 11. With this arrangement, the cable 35 is provided with a plurality of loops 43 each of which extends between the control ring 31 and a respective one of the elongate elements 11. Upon tensioning of the cable 35, the loops are caused to contract thereby pulling the elongate elements radially outwardly with respect to the control ring from the contracted condition as shown in FIG. 1, through the intermediate position shown in FIG. 2, and into the expanded condition shown in FIG. 3.

A tensioning device 50 is provided for tensioning the cable 35. The tensioning device 50 comprises a shaft 51 having a barrel portion 52 about which the cable 35 can be wound and a handle portion 53 for rotating the shaft to cause winding of the cable about the barrel portion 52. The handle 53 incorporates two diametrally opposed hooks 55, either one of which can be engaged with one of the elongate elements 11 in the manner shown in FIG. 3 to prevent rotation of the shaft 51 when the cable is wound around the barrel and thereby prevent unintentional unwinding of the cable to release the elongate elements from the expanded condition.

Figure 4:
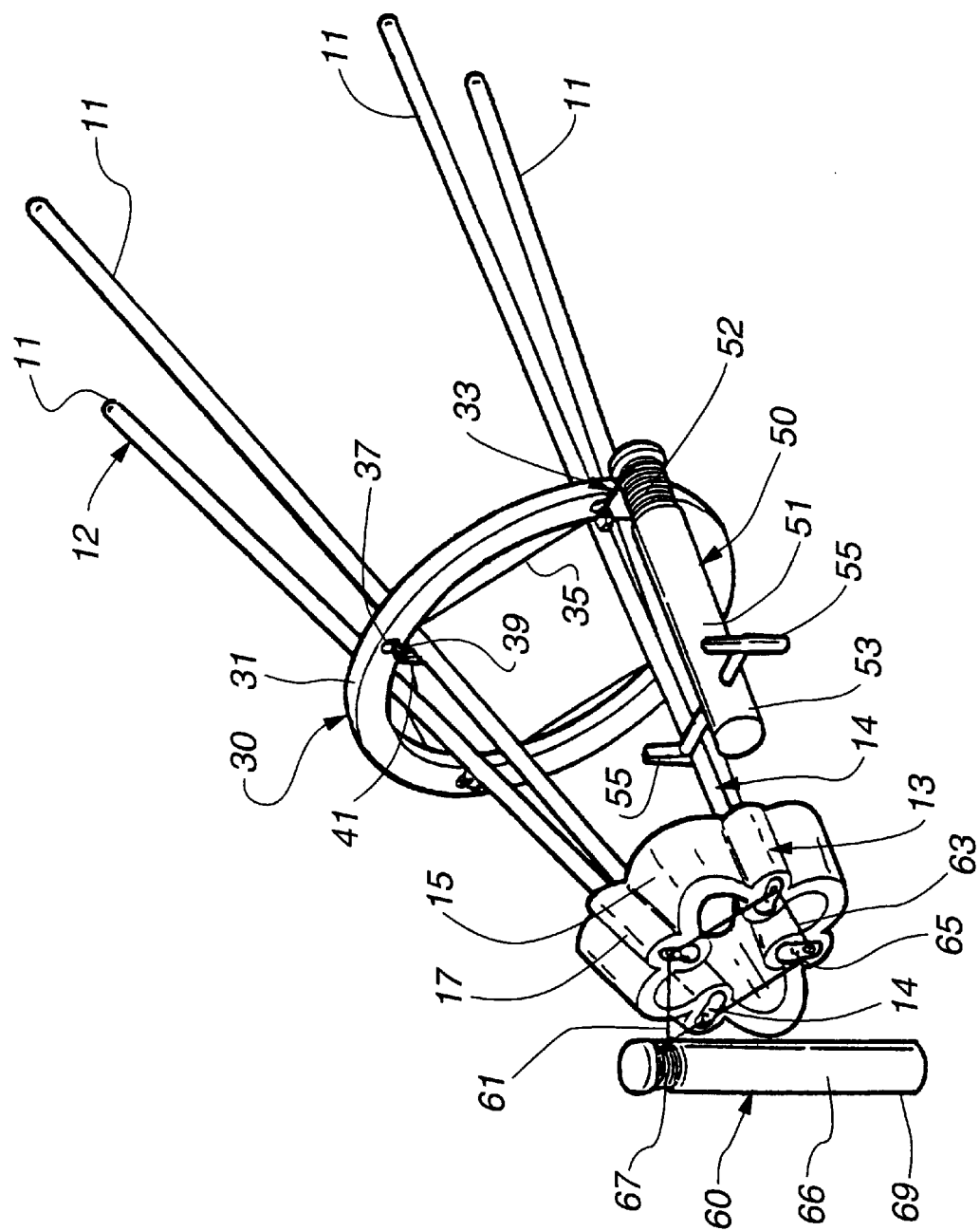
FIG. 4 is a view similar to FIG. 3 with the exception that the vaginal speculum is shown in a further expanded condition.

A supplementary control means 60 is provided for selectively contracting the second end sections 14 of the elongate elements 11 and thereby further expanding the first end sections 12 thereof, as shown in FIG. 4 of the drawings. The supplementary control means 60 comprises a cable 61 threaded through apertures 63 in lugs 65 provided on the ends of the elongate elements 11 which extend beyond the sleeve portions 17 in the retaining means 13. Tensioning of the cable 61 draws the second end sections 14 of the elongate elements 11 inwardly. The cable 61 is tensioned by a supplementary tensioning device 63 comprising a shaft 66 having a barrel portion 67 and a handle 69. The cable 61 is tensioned by rotating the shaft 65 to cause the cable 61 to wind around the barrel portion 67.

The supplementary control means 60 may well not be used in normal circumstances but rather only in circumstances where additional dilation of a vagina is necessary.

Operation of the vaginal speculum 10 will now be described with reference to FIGS. 5 to 8 of the drawings. The relevant anatomical arrangement of a patient 70 on whom the vaginal speculum is used is also shown. The anatomical arrangement of the patient 70 comprises a vagina 71 having a vaginal wall 72 extending between an outer end 73 and an inner end 75 into which a cervix 77 projects.

Figure 5:
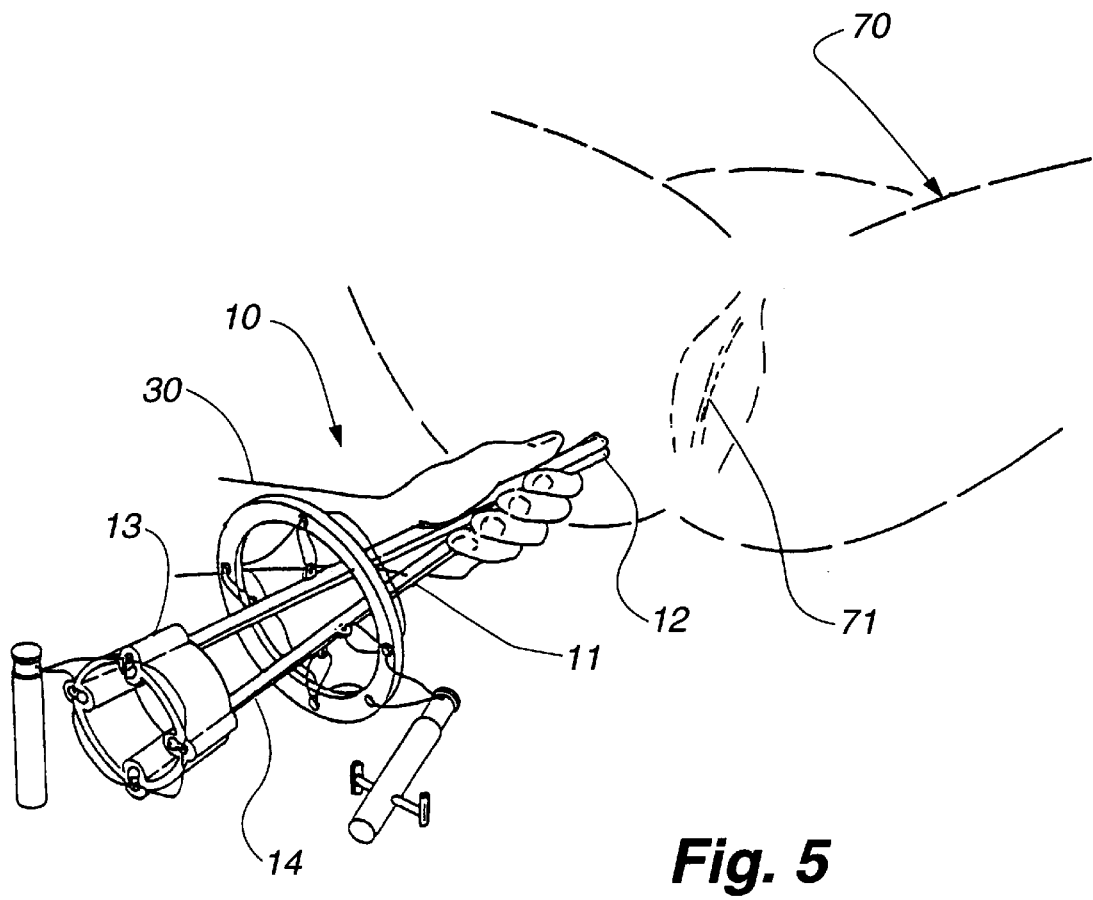
FIG. 5 is a schematic view showing the vaginal speculum prior to insertion into a vagina.
Figure 6:
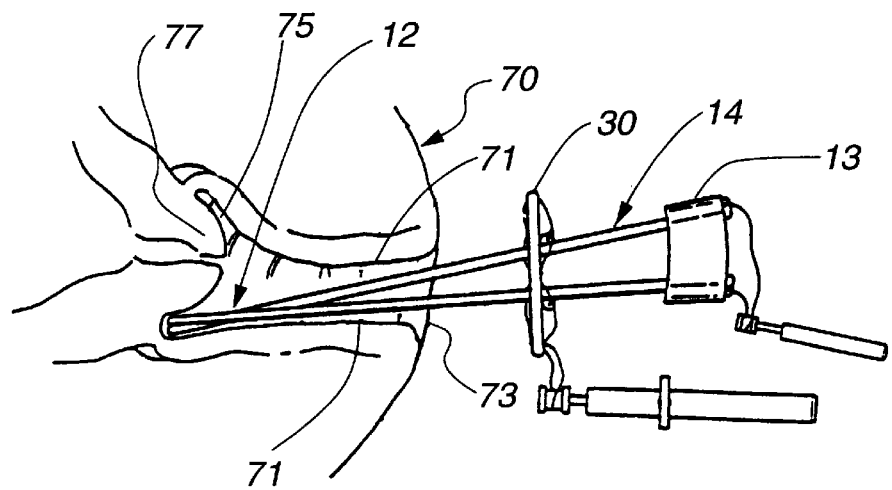
FIG. 6 is a schematic view showing the vaginal speculum in position in the vagina prior to expansion thereof into the expanded condition.

With the vaginal speculum 10 in the contracted condition, the first end sections 12 of the elongate elements 11 are presented to the vagina 71, as shown in FIG. 5. The elongate elements 11 are inserted into the vagina 71 and typically locate in a region at the inner end thereof 75 adjacent the cervix 77, as shown in FIG. 6 of the drawings.

Figure 7:
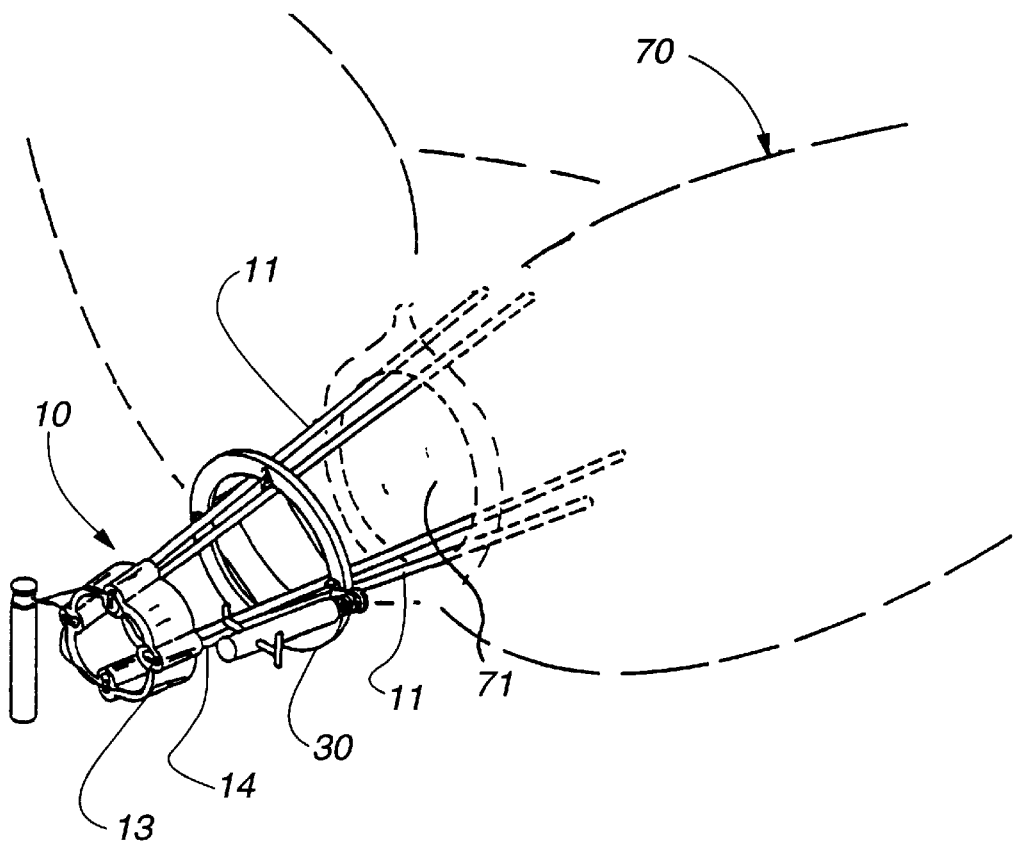
FIG. 7 is a schematic view showing the vaginal speculum in an expanded condition in the vagina to cause dilation thereof.
Figure 8:
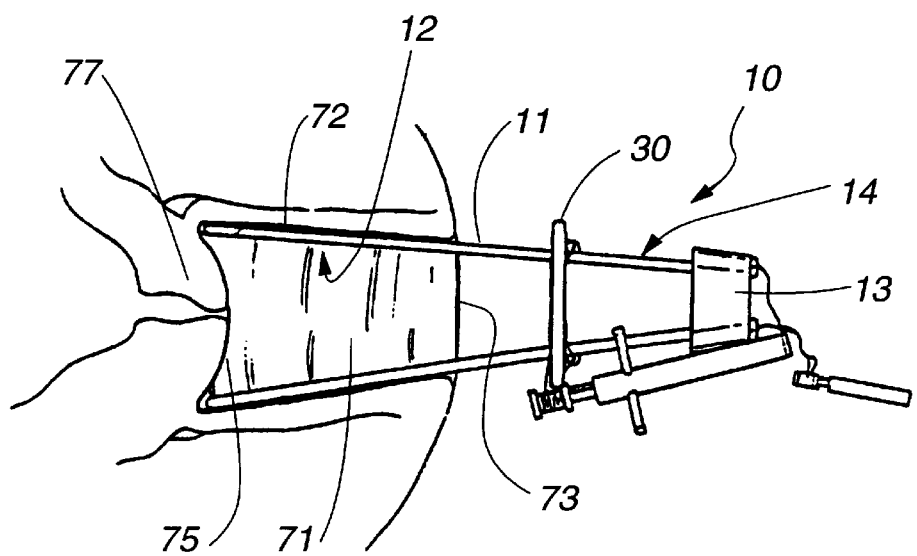
FIG. 8 is a side view of the arrangement shown in FIG. 7.

The control device 30 is then operated to move the elongate elements 11 from the contracted condition towards the expanded condition. As the elongate elements 11 move towards the expanded condition, they assume a circumferentially spaced apart arrangement and bear against the vaginal walls 72 at circumferentially spaced locations, as best illustrated in FIG. 7 of the drawings. Continued outward movement of the elongate elements 11 causes dilation of the vagina 71 and thereby provides a clear view of the cervical region. In the expanded condition, the four elongate elements 11 define therebetween a central region of an open-ended elongate shape through which the vaginal walls and cervical region can be inspected. This also provides good access for an instrument such as a swab. Further, access is available through the spaces between adjacent elongate elements, thereby allowing an angular approach to the dilated vagina. The speculum 10 ensures that the vagina 71 is maintained in the dilated condition throughout the procedure.

The resiliently flexible nature of the elongate elements 11 allows them to deflect slightly to provide somewhat uniform pressure on the vaginal walls 72 along the length thereof.

At the completion of the gynaecological procedure, the elongate elements 11 can be returned to the contracted condition by unwinding the cable from the tensioning device 50. The pressure applied to the elongate elements 11 causes them to move towards the contracted condition as the cable is unwound. The speculum can be withdrawn once it has contracted sufficiently.

Figure 9:
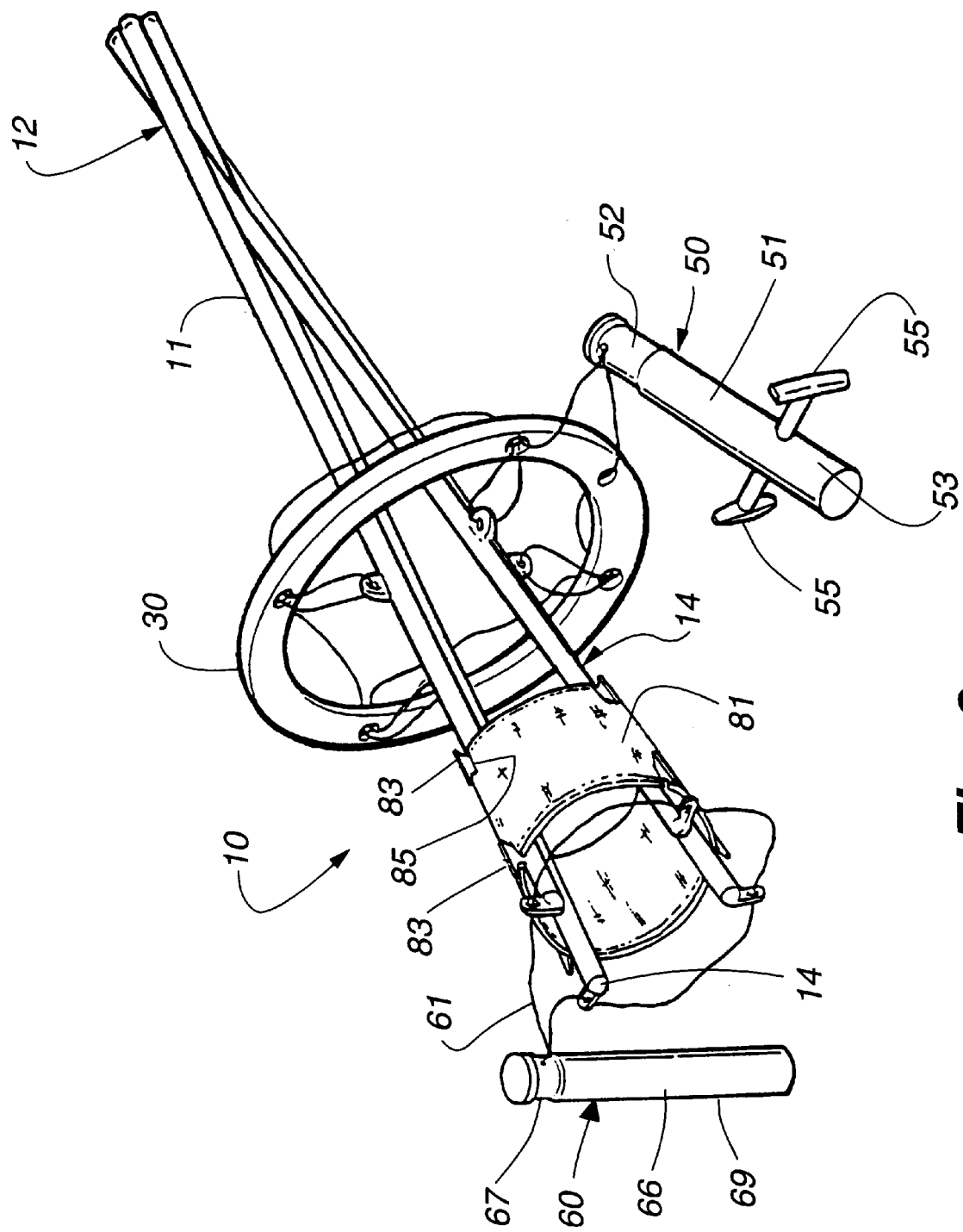
FIG. 9 is a perspective view of a vaginal speculum according to a second embodiment.

Referring now to FIG. 9 of the drawings, the speculum 10 according to the second embodiment is somewhat similar to that of the first embodiment with the exception of the retaining means 13. In this embodiment, the retaining means 13 comprises a band 81 of elastic material which is secured to each elongate element 11 between two longitudinally space retaining lugs 83 mounted thereon. The band 81 has a slit 85 which accommodates each retaining lug 83 to thereby prevent sliding movement of the elongate element around the band. Operation of the vaginal speculum according to the second embodiment is substantially the same as that according to the first embodiment.

From the foregoing, it is evident that the two embodiments provide a simple yet highly effective vaginal speculum. The vaginal speculum is convenient to install in that it is merely positioned in the contracted condition and then inserted into the vagina. When in the expanded condition, the vaginal speculum allows good vision and convenient access along the central region thereof defined between the circumferentially spaced elongate elements. The curved contact walls of the elongate elements minimise discomfort and the thin profile of the elongate elements minimises the extent to which the vaginal walls are obstructed from vision.

It should be appreciated that the scope of the invention is not limited to the scope of the two embodiments described.

I claim:

1. Apparatus for dilating body cavity comprising:

at least two elongate elements positioned in generally side-by-side relationship and movable laterally with respect to each other between a contracted condition wherein first end sections of the elongate elements are closely adjacent one another for insertion into the body cavity and an expanded condition wherein the first end sections of the elongate elements are circumferentially spaced apart for dilating the body cavity; and a control means for selectively moving the elongate elements from one of said contracted and expanded conditions to the other of said contracted and expanded conditions, said control means including:

a control ring encircling the elongate elements, and adjustment means extending between adjacent elongate elements and the control ring, the adjustment means being operable to move said elongate elements with respect to the control ring and thereby moving said elongate elements from said one condition to said other condition, the adjustment means including a funicular element laced between the control ring and said elongate elements whereby tensioning of the funicular element draws said elongate elements outwardly towards the ring.

2. Apparatus according to claim 1 wherein there are four elongate elements.

3. Apparatus according to claim 1 wherein the elongate elements are thin in profile.

4. Apparatus according to claim 1 wherein the elongate elements are each of rounded cross-section.

5. Apparatus according to claim 1 wherein the elongate elements are firm yet resiliently flexible along the length thereof.

6. Apparatus according to claim 1 wherein the elongate elements normally occupy the contracted condition and operation of the control means causes movement of the elongate elements from the contracted condition to the expanded condition.

7. Apparatus according to claim 1 wherein there is provided a tensioning device around which the funicular element can be wound for tensioning thereof.

8. Apparatus according to claim 7 wherein said tensioning device further includes a locking means for selectively locking the tensioning device against rotation in the reverse direction to prevent unwinding the funicular element.

9. Apparatus according to claim 1 wherein a retaining means is provided for retaining the elongate elements in said side-by-side relationship.

10. Apparatus according to claim 9 wherein the retaining means is disposed on a second end section of the elongate elements opposite to said first end section thereof.

11. Apparatus according to claim 10 wherein said retaining means comprises a closed loop.

12. Apparatus according to claim 9 wherein said retaining means comprises a closed loop.

13. Apparatus according to claim 12 wherein the closed loop is flexible.

14. Apparatus according to claim 13 wherein the closed loop is resiliently flexible.

* * * * *